(12) United States Patent
Perring et al.

(10) Patent No.: US 8,821,847 B2
(45) Date of Patent: Sep. 2, 2014

(54) PERFUME COMPOSITIONS

(71) Applicant: Givaudan Nederland Services B.V., Naarden (NL)

(72) Inventors: Keith Douglas Perring, Ashford (GB); Michael Gordon Evans, Canterbury (GB); Alan Forbes Provan, Ashford (GB); David Jonathan Bradshaw, Ashford (GB); John Martin Behan, Ashford (GB)

(73) Assignee: Givaudan Nederland Services B.V., Naarden (NL)

( * ) Notice: Subject to any disclaimer, the term of this patent is extended or adjusted under 35 U.S.C. 154(b) by 0 days.

(21) Appl. No.: 13/861,866

(22) Filed: Apr. 12, 2013

(65) Prior Publication Data

US 2013/0230479 A1    Sep. 5, 2013

Related U.S. Application Data

(63) Continuation of application No. 12/375,733, filed as application No. PCT/GB2007/002986 on Aug. 3, 2007, now abandoned.

(30) Foreign Application Priority Data

Aug. 5, 2006    (GB) .................................... 0615580.8

(51) Int. Cl.
*A61L 9/04* (2006.01)
*A61L 11/00* (2006.01)
*A61K 8/18* (2006.01)
*A61L 9/01* (2006.01)
*C11B 9/00* (2006.01)
*A61L 15/46* (2006.01)
*A01K 1/015* (2006.01)

(52) U.S. Cl.
CPC . *A61L 11/00* (2013.01); *A61L 9/01* (2013.01); *A61L 2300/216* (2013.01); *C11B 9/0061* (2013.01); *A61L 15/46* (2013.01); *A01K 1/0152* (2013.01); *A61L 2300/204* (2013.01)

USPC ................ 424/76.4; 424/76.6; 512/8; 512/9; 512/11

(58) Field of Classification Search
USPC ........................... 424/76.4, 76.6; 512/8, 9, 11
See application file for complete search history.

(56) References Cited

U.S. PATENT DOCUMENTS

| | | | |
|---|---|---|---|
| 6,025,186 A | 2/2000 | Kirk et al. | |
| 2009/0257974 A1 | 10/2009 | Evans et al. | |
| 2013/0039876 A1* | 2/2013 | Perring et al. | ............... 424/76.6 |
| 2013/0039877 A1* | 2/2013 | Perring et al. | ............... 424/76.6 |

FOREIGN PATENT DOCUMENTS

| | | |
|---|---|---|
| WO | 9630470 A | 10/1996 |
| WO | 2004009051 A2 | 1/2004 |
| WO | 2004098667 A | 11/2004 |

OTHER PUBLICATIONS

International Search Report for PCT/GB2007/002986 dated Dec. 7, 2007.
Written Opinion of the International Searching Authority dated Dec. 7, 2007.
CAS Registry No. 140-11-4 for "benzyl acetate", one page, (Retrieved from https://scifinder.cas.org/scifinder/view/scifinder/scifinderExplore.jsf on Oct. 6, 2011),in US Office Action dated Oct. 13, 2011.
CAS Registry No. 120-57-0 for "heliotropin", one page, (Retrieved from https://scifinder.cas.org/scifinder/view/scifinder/scifinderExplore.jsf on Oct. 6, 2011), in US Office Action dated Oct. 13, 2011.
CAS Registry No. 60-12-8 for "2-phenylethanol", one page, (Retrieved from https://scifinder.cas.org/scifinder/view/scifinder/scifinderExplore.jsf on Oct. 6, 2011), in US Office Action dated Oct. 13, 2011.

* cited by examiner

*Primary Examiner* — Aradhana Sasan
(74) *Attorney, Agent, or Firm* — Norris McLaughlin & Marcus PA

(57) ABSTRACT

Perfume compositions effective against urine malodor and having a low odor, comprise between 20% and 50% of perfume ingredients comprising at least 15% by-weight of N-ethyl-N-(3-methylphenyl) propanamide.

10 Claims, No Drawings

PERFUME COMPOSITIONS

This application is a continuation of U.S. application Ser. No. 12/375,733 filed Jan. 30, 2009, which is a 371 application of PCT/GB2007/002986 filed Aug. 3, 2007, which claims priority to the GB application 0615580.8 filed Aug. 5, 2006.

FIELD OF THE INVENTION

This invention relates to perfume compositions, to consumer products containing such perfume compositions, and to the use of such perfume compositions to provide deodorant effects including in particular inhibiting and ameliorating the odour of urine. The invention is particularly concerned with perfume compositions that inhibit the bacterial generation of ammonia from urea.

BACKGROUND TO THE INVENTION

The unpleasantness of urine malodour is an age-old problem. When urine is excreted into absorbent articles such as clothing, diapers or incontinence pads, or onto floors surrounding urinals or WC bowls, an ammoniacal malodour may often be detected within a short time. The same problem occurs in pet litter, and may of course be relevant anywhere in the house for households including cats or dogs, etc.

Urine is a clear, transparent fluid that normally has an amber color, and when fresh is generally of low odour. The average amount of urine excreted by a human in 24 hours is about 1,200 cubic centimeters. Chemically, urine is mainly an aqueous solution of sodium chloride and organic substances such as urea and uric acid. Normally, it contains about 960 parts of water to 40 parts of solid matter. Many hundreds of different mineral salts and organic compounds are present in urine, albeit at trace levels for a significant proportion of these. The pH of normal urine is between 4.5 and 7.8, but usually it ranges between 5.0 and 6.0, due to obligatory excretion of acid produced every day.

The major components of urine malodour are: ammonia, volatile fatty acids (primarily acetic, propionic, butyric, formic); volatile sulphur compounds e.g hydrogen sulfide ($H_2S$) and methyl sulphides such as methyl mercaptan ($CH_3SH$); other nitrogenous compounds such as indole, skatole, pyridine, pyrrole, ethylamine; various other volatiles including benzyl alcohol, phenol, p-cresol, ethanol, methanol, acetone, methyl ethyl ketone, acetaldehyde, propionaldehyde, pentanone, heptanone, propanol, butanol, octanol. These odourous molecules are mainly produced as a result of the bacterial degradation of exogenous materials such as urea and uric acid found in urine, though trace levels of certain materials may reflect materials found in the diet or in the environment. The nitrogenous bases, in particular ammonia, contribute significantly to the malodour recognised by most people from used diapers or other hygiene products such as adult incontinence products. This malodour arises at least partly from the bacterially mediated degradation of urea, from the metabolism of microorganisms present on the skin or from the urogenital tract, for example from the growth of *Proteus* and *Micrococcus* species. All strains of *Proteus* spp. form the enzyme urease during their metabolism. Urease has the ability to rapidly break down urea (constituting about 2% of human urine) into ammonia causing unpleasant odour. The headspace composition above stale urine comprises a variety of materials, but the dominant malodour contributor under most conditions is invariably ammonia. Any route to reduction in the amount of ammonia present above urine is therefore of possible utility in product sectors associated with sanitation, hygiene, and incontinence. Several approaches are known in the art that address this need.

Antimicrobial agents used in personal products are designed to reduce the population, inhibit the growth or diminish the metabolic activities of microorganisms associated closely with the body—on the surface of the skin, in mucosal surfaces, in the urogenital tract, etc. Typical agents of this nature include triclosan (2',4,4'-trichloro-2-hydroxydiphenyl ether) and zinc oxide which are well known to exert antimicrobial and deodourant effects. The use of common deodourant actives results in a non-selective antimicrobial action exerted upon most of the skin's natural microflora. Certain perfume components and mixtures thereof may contribute to such antimicrobial effects. For example, published U.S. application US2004266302 relates to a disposable absorbent article containing an encapsulated antimicrobial essential oil for odour control.

WO 2002/47472 relates to products and methods that utilise a urease inhibitor formed from a polyanionic, and preferably amine-based, chelating agent and a divalent heavy metal ion, to prevent or minimize ammonia odour produced by the degradation of urea in secreted or excreted body fluids. Similarly WO 97/46187 relates to absorbent articles in particular sanitary napkins and panty liners having an odour control system comprising a polyfunctionally substituted aromatic chelating agent for improved odour control.

Much of the art is concerned with the use of odour absorbent materials. For example, WO 2001/80915 relates to absorbent articles that comprise a cationic polysaccharide, preferably chitosan material, and silicate. These articles claim to deliver improved odour control performance (synergistic odour reduction) and improved fluid handling properties/absorption performance WO 94/25077 relates to odour control through an absorbent article containing a boric acid/sodium tetraborate buffer. EP 509409 relates to malodour control though the design of an absorbent article containing a deodourizing blend of anhydrous, non-buffer blend of at least basic and pH neutral odour absorbing particles. U.S. Pat. No. 6,031,147 discloses an absorbent product comprising a hydrogel-forming polymeric absorbent material and a surface-active agent such as ethoxylated sorbitan monooleate, having a hydrophilic/lipophilic balance of less than about 12.

WO 99/06078 describes absorbent materials containing cyclodextrin as an odour control material. WO 98/26808 describes odour control provided by a combination of a material that inhibits the formation of odour (and has at least one attribute selected from the group consisting of antimicrobial activity, urease inhibition activity, pH adjustment activity) and an odour-absorbing material for objectionable odour molecules selected from the group consisting of cyclodextrin, zeolite, activated carbon, kieselguhr, acid salt forming materials and mixtures thereof. The scent signal is provided by cyclodextrin/perfume inclusion complexes and/or matrix perfume microcapsules to assure the wearer that the product is working.

WO 00/51652 describes the use of oxidising agents such as a peroxyacid in combination with an odour-absorbing agent such as silica and/or zeolite. WO2003/051413 and WO 2003/051410 relate to a fibrous absorbent material or cellulose fibers treated with a carboxylic acid based odour control agent.

Perfumes have long been recognised as beneficial in hygiene and sanitary sectors. WO 98/25562 describes a diaper design that contains perfume zones and microcapsules as release agents to provide odour control. US 2003/072733 describes a process for absorbing moisture and/or malodour while providing a fragrance to the surrounding ambience. WO 2005/044320 relates to a dual purpose volatile substance controlling composition comprising a sorbent and a fragrance component designed to control malodours including those resulting from bodily fluids. The design involves volatile substance sorption directly linked to fragrance release.

Perfumes may simply mask malodours. WO 2004/10325 describes sanitary absorbent articles comprising a non-aqueous volatile cooling agent such as menthyl lactate or perfume. WO 2004/108177 describes the incorporation of a starch-encapsulated accord into products that releases perfume to minimise odour.

Perfume compositions have been disclosed which exhibit effective deodourant action for specific malodours. For example, WO 00/01356 describes certain perfume components and compositions thereof, useful in reducing or preventing body malodour. The perfume components (or compositions comprising the perfume components) are described as inhibiting coryneform bacteria that are capable of catabolising fatty acids and are responsible for the production of short chain fatty acid malodour. In this way, the perfume components (or compositions thereof) in-use produce a deodourant effect.

WO 2004/098666 and WO 2004/098667 both disclose perfumes for use in controlling odours associated with non-axillary bodily fluids. These perfumes were based on mixtures of musks and salicylates and designed to exhibit low odour intensities more suitable for use in intimate products.

However, many of the deodourant perfumes disclosed in the art have relatively high odour intensities that are unsuitable for use in the sanitary or incontinence product sector, may offer only a limited range of odour directions, and/or are not effective in counteracting or inhibiting ammonia malodour.

In spite of the above mentioned disclosures there still exists a need for cost-effective products that combat urine-derived malodour more efficiently, both from the perspective of malodour prevention as well as malodour amelioration, and do not suffer from the potential disadvantage of excessive perfume odour intensity.

It has now been surprisingly found that particular perfume compositions are capable of inhibiting the development of ammonia from urea and are effective in counteracting urine malodour in spite of exhibiting relatively low perfume odour intensities.

SUMMARY OF THE INVENTION

In one aspect, this invention provides a perfume composition that inhibits the formation of urine malodour, and are effective in ameliorating the perception of urine malodour if present. Such perfume compositions comprise between 20% and 50% by weight of perfume ingredients drawn from the following groups:

i) at least 15% by weight of N-ethyl-N-(3-methylphenyl) propanamide;

ii) 0-30% Group A materials, consisting of (3Z)-hex-3-enyl acetate; 3-(1,3-benzodioxol-5-yl)-2-methylpropanal; (3Z)-hex-3-en-1-ol; 1-[4-(methyloxy)phenyl]ethanone; 3-methyl-5-phenylpentan-1-ol; 5-heptyldihydrofuran-2 (3H)-one; phenylmethyl acetate; 2-(4-methylcyclohex-3-en-1-yl)propan-2-ol; (3E)-4-(2,6,6-trimethylcyclohex-2-en-1-yl)but-3-en-2-one; (3E)-4-(2,6,6-trimethylcyclohex-1-en-1-yl)but-3-en-2-one; 4-hydroxy-3-(methyloxy)benzaldehyde; 1-methyl-3-(2-methylpropyl)cyclohexanol; 7,9-dimethyl-spiro[5.5]undecan-3-one; perfume 1 being Lavandin AB8381™; methyl 2,4-dihydroxy-3,6-dimethylbenzoate; 3,7-dimethyloctan-1-ol; 2-(methyloxy)-4-propylphenol; perfume 2 being Rosenta AB8428™; 1-{[(1R,2S)-2-(1,1-dimethylethyl)cyclohexyl]oxy}butan-2-ol; perfume 3 being Headspace Freesia AB7254A™; 5-hexyldihydrofuran-2 (3H)-one; prop-2-enyl[(2-methylbutyl)oxy]acetate; 1,3-benzodioxole-5-carbaldehyde; [4-(1-methylethyl)cyclohexyl] methanol; 2-hexylcyclopent-2-en-1-one; methyl (2E)-3-phenylprop-2-enoate; 2,6-dimethyloct-7-en-2-ol; 2-methyl-3-[4-(1-methylethyl)phenyl]propanal;

iii) 0-30% Group B materials, consisting of 2-phenylethanol, 3,7-dimethyloctan-3-ol (tetrahydro linalol), 2-(methyloxy)-4-[(1E)-prop-1-enyl]phenyl acetate; 4-(methyloxy) benzaldehyde; (2E)-1-(2,6,6-trimethylcyclohex-2-en-1-yl) but-2-en-1-one; perfume 4 being Bergamot AB8392™, (3E)-3-methyl-4-(2,6,6-trimethyleyclohex-2-en-1-yl)but-3-en-2-one; cyclopentadecanone; cyclohexadecanolide; prop-2-enyl 3-cyclohexylpropanoate; 3-[3-(1-methylethyl)phenyl]butanal; (3Z)-hex-3-enyl methyl carbonate; (1-methyl-2-{[(1S, 3R,5R)-1,2,2-trimethylbicyclo[3.1.0]hex-3-yl] methyl}cyclopropyl)methanol; [3,3-bis(methyloxy)propyl] benzene; perfume 5 being Coumarex I Mod™; tricyclo [5.2.1.0$^{\{2,6\}}$]dec-4-en-8-yl propanoate.

In another aspect, the invention relates to a method of preventing or ameliorating urine malodour comprising bringing into contact with urine or urine residues an effective amount of a perfume composition according to the invention.

Preferred perfume compositions comprise at least 2 Group A materials, even more preferred comprise at least 3, and most preferred comprise 5 or more Group A ingredients, with the proviso that at least 0.3% of a material must be present before it may be considered to contribute significantly towards the efficacy of the compositions i.e. materials present at concentrations below 0.3% w/w are ignored in the calculation of the number of Group A ingredients in the composition. However, for the avoidance of doubt, materials present at concentrations below 0.3% w/w do contribute to the calculation of the total amount of Group A and Group B materials.

For the purposes of this invention a perfume composition is defined as a mixture of perfume ingredients, if desired mixed with or dissolved in a suitable solvent or solvents and/or mixed with a solid substrate. Perfume ingredients are well known to those skilled in the art, and include those mentioned, for example, in S. Arctander, Perfume and Flavor Chemicals (Montclair, N.J., 1969), in S. Arctander, Perfume and Flavor Materials of Natural Origin (Elizabeth, N.J., 1960) and in "Flavor and Fragrance Materials—1991", Allured Publishing Co. Wheaton, Ill. USA. Perfume ingredients may include natural products such as extracts, essential oils, absolutes, resinoids, resins, concretes etc., and also synthetic substances such as hydrocarbons, alcohols, aldehydes, ketones, ethers, acids, esters, acetals, ketals, nitriles, etc., including saturated and unsaturated compounds, aliphatic, macrocyclic and heterocyclic compounds.

References herein to the percentage by weight of perfume ingredients means relative to the total weight of perfume ingredients in the perfume composition and includes materials that are used within perfumery as vehicles or solvents for other perfume ingredients, for example dipropylene glycol, isopropyl myristate, benzyl benzoate, diethyl phthalate, triacetin and triethyl citrate.

Perfumes constructed according to the above design provide effective urease inhibition without exhibiting strong odour intensities (as indicated by tests described below) and also are able to counteract urine malodour olfactorily.

In a further aspect, the invention provides a perfumed consumer product comprising a perfume composition in accordance with the invention. For the purposes of this invention a consumer product comprises a solid, liquid or soft solid formulation especially for use in or on a substrate such as skin, hair (including fur), clothing or hard surface. Examples of such products include bathroom and kitchen cleaners, carpet cleaners, polishes, personal body refreshers and deodourants, pet deodourants, in a variety of formats such as liquids (particularly as delivered by trigger sprays or aerosols), gels and powders, all of which are well known in the art. Another consumer product relevant to the present invention is pet litter.

In such consumer products as little as 0.1% by weight of the perfume composition in the product will suffice.

The invention also covers use of a perfume composition according to the invention for the purpose of inhibiting urea breakdown to form ammonia. Preferred features of this aspect are as discussed below in connection with the perfume composition of the invention. A concomitant effect of the inhibition of ammonia production is that pH remains relatively constant, or at least the rate of increase of pH is much lower than in the absence of the perfume composition. Such pH control may be of indirect benefit in areas other than malodour management.

In a further aspect, the invention provides an article suitable for preventing or ameliorating urine malodour, comprising an effective mount of a perfume composition according to the invention.

Such articles of manufacture such as diapers, incontinence pads, hygienic body wipes, and catamenials including sanitary pads and sanitary towels may all benefit from the incorporation of perfumes of the invention. Perfume compositions of the invention may be incorporated into or onto such articles by any suitable means known in the art, for example by bringing them into contact with adsorbents present in such articles, although they be used in association with a wide variety of elements of such articles. It may sometimes be advantageous to encapsulate the perfumes of the invention prior to incorporation into such articles.

Perfume Ingredients of the Invention

Perfumes formulated to the guidelines described herein will maintain the pH of a urea-supplemented microbial suspension (as described below in Example 2) at a pH that is at least 1.2 pH units lower than that of a non-perfumed control. It is believed that this difference in pH is directly correlated to a decrease in ammonia production. It is highly desirable that the effect is achieved at sub-inhibitory growth levels. Two groups of perfume ingredients have been identified. Group A materials have the highest efficacy, but Group B may be used in place of a fraction of the Group A materials where this is desirable in order to achieve the right balance of hedonic properties, anti-microbial action and sensory-derived malodour counteraction. An amide, N-ethyl-N-(3-methylphenyl) propananoide, is highly active with respect to urease inhibitory efficacy, but for the purposes of this invention is treated separately from the Group A ingredients since it exhibits low odour. It is known in the industry under the tradename Agarbois™ (supplier: Givaudan).

Group A ingredients are listed below, where names in parentheses represents equivalent names—either trivial names commonly used within the fragrance and flavour industry, or tradenames that are sources for the material cited.

Group A Materials:
(3Z)-hex-3-enyl acetate (cis-3-hexenyl acetate),
3-(1,3-benzodioxol-5-yl)-2-methylpropanal [Helional™ (IFF)],
(3Z)-hex-3-en-1-ol (cis-3-hexenol)
1-[4-(methyloxy)phenyl]ethanone (paramethoxy acetophenone),
3-methyl-5-phenylpentan-1-ol [Mefrosol™(G)],
5-heptyldihydrofuran-2(3H)-one (undecalactone gamma),
phenylmethyl acetate (benzyl acetate),
2-(4-methylcyclohex-3-en-1-yl)propan-2-ol (terpineol alpha),
(3E)-4-(2,6,6-trimethylcyclohex-2-en-1-yl)but-3-en-2-one (ionone alpha),
(3E)-4-(2,6,6-trimethylcyclohex-1-en-1-yl)but-3-en-2-one (ionone beta),
4-hydroxy-3-(methyloxy)benzaldehyde (vanillin),
1-methyl-3-(2-methylpropyl)cyclohexanol [Rossitol™ (G)],
N-ethyl-N-(3-methylphenyl)propanamide [Agarbois™ (G)],
7,9-dimethylspiro[5.5]undecan-3-one [Dispirone™ (G)],
perfume 1 being Lavandin AB8381™,
methyl 2,4-dihydroxy-3,6-dimethylbenzoate (moss oakmoss synthetic),
3,7-dimethyloctan-1-ol (tetrahydrogeraniol),
2-(methyloxy)-4-propylphenol (dihydroeugenol),
perfume 2 being Rosenta AB8428™,
1-{[(1R,2S)-2-(1,1-dimethylethyl)cyclohexyl]oxy}butan-2-ol [Amber Core™ (G)],
perfume 3 being Headspace Freesia AB7254™,
5-hexyldihydrofuran-2(3H)-one (decalactone gamma),
prop-2-enyl[(2-methylbutyl)oxy]acetate (Allyl amyl glycolate),
1,3-benzodioxole-5-carbaldehyde (heliotropin),
[4-(1-methylethyl)cyclohexyl]methanol [Mayol™(F)],
2-hexylcyclopent-2-en-1-one (iso-jasmone),
methyl (2E)-3-phenylprop-2-enoate (methyl cinnamate),
2,6-dimethyloct-7-en-2-ol (dihydromyrcenol),
2-methyl-[4-(1-methylethyl)phenyl]propanal (Cyclamen aldehyde).

Group B ingredients:
2-phenylethanol (phenyl ethyl alcohol);
3,7-dimethyloctan-3-ol (tetrahydrolinalol);
2-(methyloxy)-4-[(1E)-prop-1-enyl]phenyl acetate (isoeugenyl acetate);
4-(methyloxy)benzaldehyde (anisic aldehyde);
(2E)-1-(2,6,6-trimethylcyclohex-2-en-1-yl)but-2-en-1-one (damascone alpha);
perfume 4 being Bergamot AB8392™;
(3E)-3-methyl-4-(2,6,6-trimethylcyclohex-2-en-1-yl)but-3-en-2-one (Methyl ionone alpha iso);
Cyclopentadecanone[Silvanone™ (G)];
Oxacycloheptadecan-2-one (Silvanone™ (G), cyclohexadecanolide);
prop-2-enyl 3-cyclohexylpropanoate (allyl cyclo hexyl propionate);
3-[3-(1-methylethyl)phenyl]butanal [Florohydral™ (G)];
(3Z)-hex-3-enyl methyl carbonate (cis-3-hexenyl methyl carbonate);
(1-methyl-2-{[(1S,3R,5R)-1,2,2-trimethylbicyclo[3.1.0]hex-3-yl]methyl}cyclopropyl)methanol [Javanol™(G)];
[3,3-bis(methyloxy)propyl]benzene (dimethyl hydro cinnamyl);
perfume 5 being Coumarex I Mod™(IFF);
tricyclo[5.2.1.0$^{\{2,6\}}$]dec-4-en-8-ylpropanoate [Florocyclene™(G)].

Key: G=Givaudan;
IFF=International Flavours and Fragrances;
F=Firmenich wherein perfumes 1 to 5 have the following compositions:

| Ingredient | Perfume 1 | Perfume 2 | Perfume 3 | Perfume 4 | Perfume 5 |
|---|---|---|---|---|---|
| Allylamyl glycolate | 0.8 | | | | |
| Anisaldehyde | | | | | 0.3 |
| Benzophenone | | 2.0 | | | |
| Borneol | 1.0 | | | | |
| Camphene | 0.8 | | | | |
| Camphor | 9.2 | | | | |
| Caryophyllene | 4.5 | | | | |
| Cedarwood Texan oil | 0.8 | | | | |
| Cineole | 7.0 | | | | |
| Citral Diethylacetal | | | | 1.5 | |
| Citronellyl formate | | 1.8 | | | |
| Citronellyl propionate | 2.5 | | | | |
| Dihydrolinalol | 6.5 | | | | |
| Dihydro myrcenyl acetate | | | | 11.0 | |
| Dihydro Terpinyl Acetate | 13.5 | | | 31.5 | |
| 2,6-Dimethylheptan-2-ol | 2.0 | | | | |
| Dipropylene glycol | | 5.0 | | | 88.0 |
| Geranylacetate | | 5.0 | | | |
| Geranylacetone | | 1.0 | | | |
| Geranyl formate | | 1.2 | | | |
| Hercolyn DE (TM) | | 4.5 | | | |
| gamma-hexalone | | | | | 5.6 |
| beta-ionone | | 3.0 | 24.5 | | |
| Linalyl acetate | | 1.0 | | 32.0 | |
| Mefrosol (TM) | 10.0 | 14.0 | | | |
| 3-Methylbut-2-enyl benzoate | | | | | 4.5 |
| Neryl acetate | | | | 1.0 | |
| Ocimene | 1.0 | | | | |
| para-tert-butylcyclohexyl acetate | 4.5 | | | | |
| Phenyl acetaldehyde dimethylacetal | | 2.0 | | | |
| 2-phenylethyl alcohol | | 27.0 | | | |
| 2-phenylethyl phenylacetate | | 24.0 | | | |
| 2-phenylethyl salicylate | | 1.0 | | | |
| alpha-pinene | | | | 1.4 | |
| beta-pinene | | | | 6.8 | |
| Clary sage oil | | 0.8 | | | |
| gamma-terpinene | | | | 6.0 | |
| alpha-terpineol | 4.2 | | | 12.2 | |
| Terpinyl acetate | 17.9 | | | | |
| alpha-terpinyl isobutyrate | 2.5 | | | | |
| Tetrahydrogeraniol | | 1.4 | | | |
| Tetrahydrolinalol | | | 60.3 | 4.0 | |
| Tetrahydrolinalyl acetate | 4.5 | | | | |
| Minor components | 6.8 | 5.3 | 3.0 | 4.8 | 1.6 |
| Totals | 100 | 100 | 100 | 100 | 100 |

KEY
Mefrosol is 3-methyl-5-phenylpentan-1-ol
Hercolyn DE is a mixture of methyl dihydroabietate and tetrahydroabietate Particularly useful embodiments of the invention comprise perfume compositions incorporating 15% to 20% of Agarbois™, together with 5% to 10% of Group A materials and 5% to 10% of Group B materials.

Particularly preferred Group A materials are: (3Z)-hex-3-enyl acetate;

3-(1,3-benzodioxol-5-yl)-2-methylpropanal; (3Z)-hex-3-en-1-ol;

3-methyl-5-phenylpentan-1-ol; 5-heptyldihydrofuran-2(3H)-one;

phenylmethyl acetate; 2-(4-methylcyclohex-3-en-1-yl)propan-2-ol;

2,6-dimethyloct-7-en-2-ol; (3E)-4-(2,6,6-trimethylcyclohex-2-en-1-yl)but-3-en-2-one;

(3E)-4-(2,6,6-trimethylcyclohex-1-en-1-yl)but-3-en-2-one;

4-hydroxy-3-(methyloxy)benzaldehyde; 1,3-benzodioxole-5-carbaldehyde.

It has also been discovered that the presence of different perfume solvents within the composition may affect activity slightly. Embodiments incorporating triethyl citrate are preferred.

EXAMPLES

Example 1

Assessment of Odour Intensity Index (OII)

The samples are assessed by a panel of a suitable number, e.g. at least 6 expert assessors who have been trained to rate the odour intensity of a sample relative to standards.

1.5 g (+/−0.1 g) of test sample (perfume), or 1.5 g (+/−0.1 g) of benzyl acetate as a known dilution in dipropylene glycol (DPG), is placed into 7 ml white soda S.N.B. screw neck vials with 19 mm diameter necks. Benzyl acetate standards are prepared at concentrations of 5%, 10%, 15%, 20% and 25% by weight in DPG. The test samples are each coded and presented to the panel in a random order at least twice. The odour intensities of the samples are then compared with the standards and classified as being equivalent in intensity to one of the standards. The odour intensity index (OII) is then reported as 5 (or less), 10, 15, 20 or 25 (or more) where there is a panel consensus. In cases where no consensus is reached the OII is reported as a range (eg 5-10) provided the range does not exceed 5, in which case the experiment should be repeated.

Example 2

Urease Assay—Estimation of Fragrance and Fragrance Ingredients Effect on Ammonia Production The method adopted was based on the rapid method devised by C. A. Stuart, Elizabeth van Stratum and Robert Rustigan Further Studies on Urease Production by *Proteus* and Related Organisms J. Bacteriol. 1945, 49:437-444.

SSR Medium: 380 ml distilled water, 364 mg KH2PO4, 380 mg Na2HPO4, 8 g Urea, 40 mg Yeast extract, 20 ml 0.02% phenol red indicator, pH 6.8, solution filter sterilised.

Culture: Liquid culture of *P. vulgaris* NCTC4175 was prepared by adding loops of fresh culture from solid media (Tryptone Soya Agar) to sterile 0.1% special peptone solution. Absorbance of culture was adjusted to be OD610 nm>2.3

Fragrances were aseptically prepared at 2500 ppm in medium in duplicate (5 ml volumes) using solubiser Synperonic 91/10 at ratio of 1:2 fragrance: solubiliser. In addition 5 ml volumes of positive and negative controls were prepared. Positive controls and all test solutions were inoculated by adding 200 μl of prepared culture, mixed and incubated for 24 hours @37° C. No culture was added to the negative growth controls. Initially solutions were orange in colour. Urease activity can be noted by the production of a purple/red colour. The degree of urease activity/ammonia production was assessed by pH electrode.

Example 3

Perfume Compositions

Tables 1 to 3 list perfume composition examples A through to J. Examples A, B, C, E, F, H, I and J fall within the invention, examples D and G are comparatives.

TABLE 1

Perfume compositions A to D (% w/w)

| | Example A | B | C | D |
|---|---|---|---|---|
| Perfume code | 9084 | 9084A | 9084B/1 | 0049 |
| Agarbois ™ | 16 | 16 | 16 | 14 |
| Amberlyn Super ™10% DEP | 0.2 | 0.1 | 0.5 | 0.5 |
| Anisic aldehyde(B) | 0.2 | 0.1 | 0.4 | |
| cis-3-hexenyl acetate(A) | 0.1 | | 0.2 | |
| cis-3-hexenyl acetate 10% DEP(A) | | 0.4 | | |
| cis-3-hexenyl salicylate extra | 0.5 | 0.3 | 1 | 0.7 |
| Coumarex I mod ™(B) | 0.5 | 0.2 | 0.8 | |
| Decalactone gamma(A) | 0.3 | 0.2 | 0.6 | |
| Dimethyl hydro cinnamyl(B) | 0.2 | 0.1 | 0.4 | |
| Dispirone ™(A) | 0.1 | | 0.1 | |
| Ethylene brassylate | 3 | 3 | 3 | 6 |
| Florhydral ™(B) | 0.1 | | 0.1 | |
| Florhydral 10% DEP(B) | | 0.5 | | |
| Florosa ™ | 0.4 | 0.3 | 1 | 0.8 |
| Habanolide ™ | 2 | 1 | 3 | 3 |
| Helional ™(A) | 0.4 | 0.2 | 0.7 | |
| Ionone alpha(A) | 1.2 | 0.8 | 2 | |
| Mefrosol ™(A) | 4 | 3.2 | 3.6 | |
| Methyl dihydrojasmonate | 10 | 5 | 10 | 7 |
| para-Methoxyacetophenone (A) | 0.5 | 0.2 | 0.6 | |
| Phenyl ethyl alcohol (B) | 0.5 | 0.2 | 0.7 | |
| Silvanone ™(B) | 2 | 2 | 1.4 | |
| Tetrahydrogeraniol (A) | 1 | 0.7 | 1.5 | |
| Tetrahydrolinalol (B) | 1 | 1 | 1.2 | |
| Triethyl citrate | 55.4 | 64.3 | 50.6 | 68 |
| Vanillin (A) | 0.4 | 0.2 | 0.6 | |
| Total Agarbois ™ | 16 | 16 | 16 | 14 |
| Total Group A | 8 | 5.54 | 9.7 | 0 |
| Total Group B | 4.5 | 3.65 | 5.0 | 0 |
| Total Group A + B | 12.5 | 9.19 | 14.7 | 0 |
| No of Group A materials | 7 | 3 | 7 | 0 |
| ODOUR INTENSITY INDEX* | 5-10 | 5 | 10-15 | 5 |

KEY:
(A) = class A ingredient
(B) = class B ingredient
*odour intensity based on specified benzyl acetate dilutions

TABLE 2

Perfume compositions E to G (% w/w)

| | Example E | F | G |
|---|---|---|---|
| Perfume Code | 9085 | 9085A | 0048 |
| Agarbois ™ | 15 | 17 | 10 |
| Allyl amyl glycolate (A) 10% DEP | 0.5 | 0.2 | |
| Amberlyn Super ™ | 0.2 | 0.1 | 0.2 |
| Anisic aldehyde (B) | 0.2 | 0.1 | 0.1 |
| Bangalol ™ | 0.4 | 0.2 | 0.5 |
| Bergamot AB8392 ™(B) | 1 | 0.5 | 0.5 |
| Bourgeonal ™ | 0.1 | 0.1 | 0.4 |
| cis-3-hexenol (A) 10% DEP | 0.2 | 0.1 | |
| Cyclopentadecanolide | 1 | 1 | 1 |
| Dihydromyrcenol (A) | 0.7 | 0.4 | |
| Ethylene brassylate | 6 | 4 | 7 |
| Helional ™(A) | 0.1 | 0.1 | |
| Heliotropin 10% DEP | 0.5 | 0.2 | |
| Hexyl salicylate | 2 | 0.5 | 3 |
| Ionone alpha (A) | 0.5 | 0.2 | |
| Iso Ambois ™ | 0.2 | 0.1 | 1 |
| Isobornylcyclohexanol | 1 | 0.4 | 0.5 |
| Iso-jasmone 10% DEP (A) | 0.4 | 0.2 | |
| Mayol ™ (A) | 0.4 | 0.2 | |
| Mefrosol ™(A) | 5 | 3.5 | |
| Methyl dihydrojasmonate | 10 | 5 | 6 |
| Methyl ionone alpha (B) | 0.5 | 0.2 | |
| Ortholate ™ | 0.2 | 0.1 | 0.8 |
| para-tert-butylcyclohexyl acetate | 1 | 0.5 | 1 |
| Phenyl ethyl alcohol (B) | 1 | 0.2 | 1 |
| Silvanone ™ (B) | | 2 | 1 |
| Terpineol alpha (A) | 0.2 | 0.1 | |
| Tetrahydrogeraniol (A) | 1 | 0.5 | |
| Tetrahydrolinalol (B) | 2.4 | 1 | 1 |
| Triethyl citrate | 48.1 | 61.2 | 65 |
| Vanillin (A) | 0.2 | 0.1 | |
| Total Agarbois ™ | 15 | 17 | 10 |
| Total Group A | 8.26 | 5.17 | 0 |
| Total Group B | 5.1 | 4.0 | 3.6 |
| Total Group A + B | 13.36 | 9.17 | 3.6 |
| No of Group A materials | 5 | 3 | 0 |
| ODOUR INTENSITY INDEX* | 20 | 20 | 10 |

KEY:
(A) = class A ingredient
(B) = class B ingredient
*odour intensity based on specified benzyl acetate dilutions

TABLE 3

Perfume Compositions H to J (% w/w)

| | Example H | I | J |
|---|---|---|---|
| Perfume Code | 9086/1 | 9087 | AG20 |
| Agarbois ™ | 15 | 15 | 20 |
| Amberlyn Super ™ | | 0.1 | |
| Amyl salicylate | | 0.2 | |
| Bangalol ™ | 0.5 | 0.3 | |
| Benzyl acetate (A) | | 0.5 | |
| cis-3-hexenyl acetate 10% DEP (A) | 0.4 | 0.7 | |
| cis3-hexenyl salicylate | 0.5 | 2 | |
| Coumarex I mod ™ (B) | 0.5 | | |
| Cyclamen aldehyde (A) | | 0.1 | |
| Cyclopentadecanolide | 0.5 | 2 | |
| Decalactone gamma (A) | 0.2 | | |
| Dimethyl hydro cinnamyl (B) | 0.1 | | |
| Dupical ™ 10% DEP | | 0.3 | |
| Habanolide ™ | 8.5 | 3 | |
| Helional ™(A) | 0.4 | | |
| Heliotropin (A) | 1 | 0.3 | |
| Hexyl salicylate | | 6 | |
| Ionone alpha (A) | 1 | 0.5 | |
| Ionone beta (A) | 1 | 0.5 | |
| Iso-jasmone (A) | 0.1 | | |
| Jasmopyrane forte ™ | 1 | 0.2 | |
| Javanol ™ 10% DEP (B) | 0.2 | | |
| Mayol ™(A) | | 0.6 | |
| Mefrosol ™ (A) | 2.4 | | |
| Methyl benzoate | 0.2 | 0.2 | |
| Methyl cinnamate (A) | 0.4 | 0.1 | |
| Methyl dihydrojasmonate | 6.6 | 10 | |
| Methyl ionone alpha (B) | 3.8 | | |
| Muguet AB8430 ™ | | 3 | |
| Orange Brazil pure 10% IPM | 0.1 | | |
| Ortholate ™ | 1 | | |
| Patchouli Light pure | 0.2 | | |

TABLE 3-continued

Perfume Compositions H to J (% w/w)

| | Example | | |
|---|---|---|---|
| | H | I | J |
| | \_\_\_\_Perfume Code\_\_\_\_ | | |
| | 9086/1 | 9087 | AG20 |
| Phenyl ethyl alcohol (B) | | 2 | |
| Silvanone ™ (B) | | 4 | |
| Terpineol alpha (A) | 0.5 | 0.6 | |
| Tetrahydrogeraniol (A) | 1 | 3 | |
| Tetrahydrolinalol (B) | 2.1 | 1.8 | |
| Triethyl citrate | 50.4 | 42.8 | 80 |
| Undecalactone gamma 10% DEP (A) | | 0.2 | |
| Vanillin (A) | 0.4 | | |
| Total Agarbois ™ | 15 | 15 | 20 |
| Total Group A | 8.44 | 6.29 | 0 |
| Total Group B | 6.52 | 7.8 | 0 |
| Total Group A + B | 14.96 | 14.09 | 0 |
| No of Group A materials | 9 | 7 | 0 |
| ODOUR INTENSITY INDEX* | 15 | 10 | 5 |

KEY:
(A) = class A ingredient
(B) = class B ingredient
*odour intensity based on specified benzyl acetate dilutions

TABLE 4

Results of Urease inhibition assays and Odour Intensity Index

| | Urease Inhibition Assay Results at 2500 ppm | | |
|---|---|---|---|
| Fragrance | Average pH | pH unit difference from +ve control | Odour Intensity Index |
| Example A | 7.51 | 1.58 | 5-10 |
| Example B | 7.56 | 1.53 | 5 |
| Example C | 7.44 | 1.65 | 10-15 |
| Example D | 8.62 | 0.47 | 5 |
| Example E | 7.62 | 1.47 | 20 |
| Example F | 7.62 | 1.47 | 20 |
| Example G | 8.67 | 0.42 | 10 |
| Example H | 7.52 | 1.57 | 15 |
| Example I | 7.68 | 1.41 | 10 |
| Example J | 7.44 | 1.65 | 5 |
| +ve control | 9.09 | N/A | N/A |
| −ve control | 7.00 | N/A | N/A |

The invention claimed is:

1. A perfume composition comprising between 20% and 50% of perfume ingredients by weight drawn from the following groups:
   i) at least 15% by weight of N-ethyl-N-(3-methylphenyl) propanamide;
   ii) 0-30% by weight of Group A materials, consisting of (3Z)-hex-3-enyl acetate; 3-(1,3-benzodioxol-5-yl)-2-methylpropanal; (3Z)-hex-3-en-1-ol; 1-[4-(methyloxy)phenyl]ethanone; 3-methyl-5-phenylpentan-1-ol; 5-heptyldihydrofuran-2(3H)-one; phenylmethyl acetate; 2-(4-methylcyclohex-3-en-1-yl)propan-2-ol; (3E)-4-(2,6,6-trimethylcyclohex-2-en-1-yl)but-3-en2-one; (3E)-4-(2,6,6-trimethylcyclohex-1-en-1-yl)but-3-en-2-one; 4-hydroxy-3-(methyloxy)benzaldehyde; 1-methyl-3-(2-methylpropyl)cyclohexanol; 7,9-dimethylspiro[5.5]undecan-3-one; perfume 1 being LAVANDIN AB8381™; methyl 2,4-dihydroxy-3,6-dimethylbenzoate; 3,7-dimethyloctan-1-ol; 2-(methyloxy)-4-propylphenol; perfume 2 being ROSENTA AB8428™; 1-{[(1R,2S)-2-(1,1-dimethylethyl)cyclohexyl]oxy}butan-2-ol; perfume 3 being HEADSPACE FREESIA AB7254A™; 5-hexyldihydrofuran-2(3H)-one; prop-2-enyl [2-methylbutyl)oxy]acetate; 1,3-benzodioxole-5-carbaldehyde; [4-(1-methylethyl)cyclohexyl]methanol; 2-hexylcyclopent-2-en-1-one; methyl (2E)-3-phenylprop-2-enoate; 2,6-dimethyloct-7-en-2-ol; 2-methyl-3[4-(1-methylethyl)phenyl]propanol;
   iii) 0-30% by weight of Group B materials, consisting of 2-phenylethanol; 3,7-dimethyloctan-3-ol (tetrahydro linalol), 2-(methyloxy)-4-[(1E)-prop-1-enyl]phenyl acetate; 4-(methyloxy)benzaldehyde; (2E)-1-(2,6,6-trimethylcyclohex-2-en-1-yl)but-2-en-1-one; perfume 4 being BERGAMOT AB8392™, (3E)-3-methyl-4-(2,6,6-trimethylcyclohex-2-en-1-yl)but-3-en-2-one; cyclopentadecanone; cyclohexadecanolide; prop-2-enyl 3-cyclohexylpropanoate; 3-[3-(1-methylethyl)phenyl] butanal; (3Z)-hex-3-enyl methyl carbonate; (1-methyl-2-{[(1S,3R,5R)-1,2,2-trimethylbicyclo[3.1.0]hex-3-yl] methyl}cyclopropyl)methanol; [3,3-bis(methyloxy) propyl]benzene; perfume 5 being COUMAREX I MOD™; tricycle[5.2.1.0$^{(2,6)}$]dec-4-en-8-ylpropanoate.

2. A perfume composition according to claim 1 comprising at least 2 Group A ingredients.

3. A perfume composition according to claim 1 comprising between 15% and 20% of N-ethyl-N-(3-methylphenyl)propanamide, between 5% and 10% of Group A materials, and between 5% and 10% of Group B materials.

4. A perfume composition according to claim 1 comprising Group A ingredients selected from the following:
(3Z)-hex-3-enyl acetate; 3-(1,3-benzodioxol-5-yl)-2-methylpropanal; (3Z)-hex-3-en-1-ol; 3-methyl-5-phenylpentan-1-ol; 5-heptyldihydrofuran-2(3H)-one; phenylmethyl acetate; 2-(4-methylcyclohex-3-en-1-yl)propan-2-ol; 2,6-dimethyloct-7-en-2-ol; (3E)-4-(2,6,6-trimethylcyclohex-2-en-1-yl)but-3-en-2-one; (3E)-4-(2,6,6-trimethylcyclohex-en-1-yl)but-3-en-2-one; 4-hydroxy-3-(methyloxy)benzaldehyde; 1,3-benzodioxole-5-carbaldehyde.

5. A method for preventing or ameliorating urine malodour comprising the step of: bringing into contact with urine or urine residues an effective amount of a composition according to claim 1.

6. A consumer product comprising a perfume composition according to claim 1.

7. An article adapted for preventing or ameliorating urine malodour, comprising an effective amount of a perfume composition according to claim 1.

8. An article according to claim 7 which is a catamenial article.

9. An article according to claim 7 which is an incontinence control article.

10. A method for inhibiting the formation of ammonia from urea comprising the step of: contacting urea with a perfume composition according to claim 1.

* * * * *